(12) United States Patent
Sakurai et al.

(10) Patent No.: US 7,229,455 B2
(45) Date of Patent: Jun. 12, 2007

(54) ULTRASONIC CALCULUS TREATMENT APPARATUS

(75) Inventors: Tomohisa Sakurai, Sagamihara (JP); Ryoji Masubuchi, Hamura (JP); Yoshitaka Honda, Tokorozawa (JP); Hiroo Ono, Hino (JP)

(73) Assignee: Olympus Corporation, Tokyo (JP)

( * ) Notice: Subject to any disclaimer, the term of this patent is extended or adjusted under 35 U.S.C. 154(b) by 328 days.

(21) Appl. No.: 10/223,793

(22) Filed: Aug. 20, 2002

(65) Prior Publication Data
US 2003/0045887 A1 Mar. 6, 2003

(30) Foreign Application Priority Data
Sep. 3, 2001 (JP) ............................. 2001-266251
Oct. 10, 2001 (JP) ............................. 2001-313013

(51) Int. Cl.
*A61B 17/32* (2006.01)
(52) U.S. Cl. ..................... 606/169; 606/128; 604/22
(58) Field of Classification Search ............. 606/128, 606/127, 169; 604/22
See application file for complete search history.

(56) References Cited

U.S. PATENT DOCUMENTS

| 4,275,363 A | * | 6/1981 | Mishiro et al. ............... 331/4 |
| 5,116,343 A |   | 5/1992 | Ams et al. |
| 5,151,085 A | * | 9/1992 | Sakurai et al. ............... 604/22 |
| 5,180,363 A | * | 1/1993 | Idemoto et al. .............. 604/22 |
| 5,527,273 A | * | 6/1996 | Manna et al. ................. 604/22 |
| 6,007,555 A | * | 12/1999 | Devine ........................ 606/169 |
| 6,027,515 A |   | 2/2000 | Cimino |
| 6,066,135 A | * | 5/2000 | Honda ......................... 606/39 |
| 6,077,285 A | * | 6/2000 | Boukhny ..................... 606/169 |
| 6,161,545 A |   | 12/2000 | Chow |
| 6,402,769 B1 | * | 6/2002 | Boukhny ..................... 606/169 |
| 6,425,906 B1 | * | 7/2002 | Young et al. ................. 606/169 |
| 6,517,560 B1 | * | 2/2003 | Toth et al. .................... 606/171 |

FOREIGN PATENT DOCUMENTS

| JP | 62-298346 | 12/1987 |
| JP | 02-268751 | 11/1990 |
| JP | 4-87671 | 3/1992 |
| JP | 2000-084485 | 3/2000 |

\* cited by examiner

*Primary Examiner*—Anhtuan T. Nguyen
*Assistant Examiner*—Darwin P Erezo
(74) *Attorney, Agent, or Firm*—Scully, Scott, Murphy & Presser, P.C.

(57) ABSTRACT

An ultrasonic calculus treatment apparatus includes a longitudinal-vibration piezoelectric oscillator for vibrating in the axial direction of an ultrasonic transmitting member and a torsional-vibration piezoelectric oscillator for vibrating about the axial direction, and further includes driving circuits for driving the piezoelectric oscillators at respective resonance frequencies and a mode selection switch for permitting the oscillators to vibrate independently or in combination, so that lithotripsy can be performed effectively in accordance with the size of a calculus or a function of an operating tool.

6 Claims, 14 Drawing Sheets

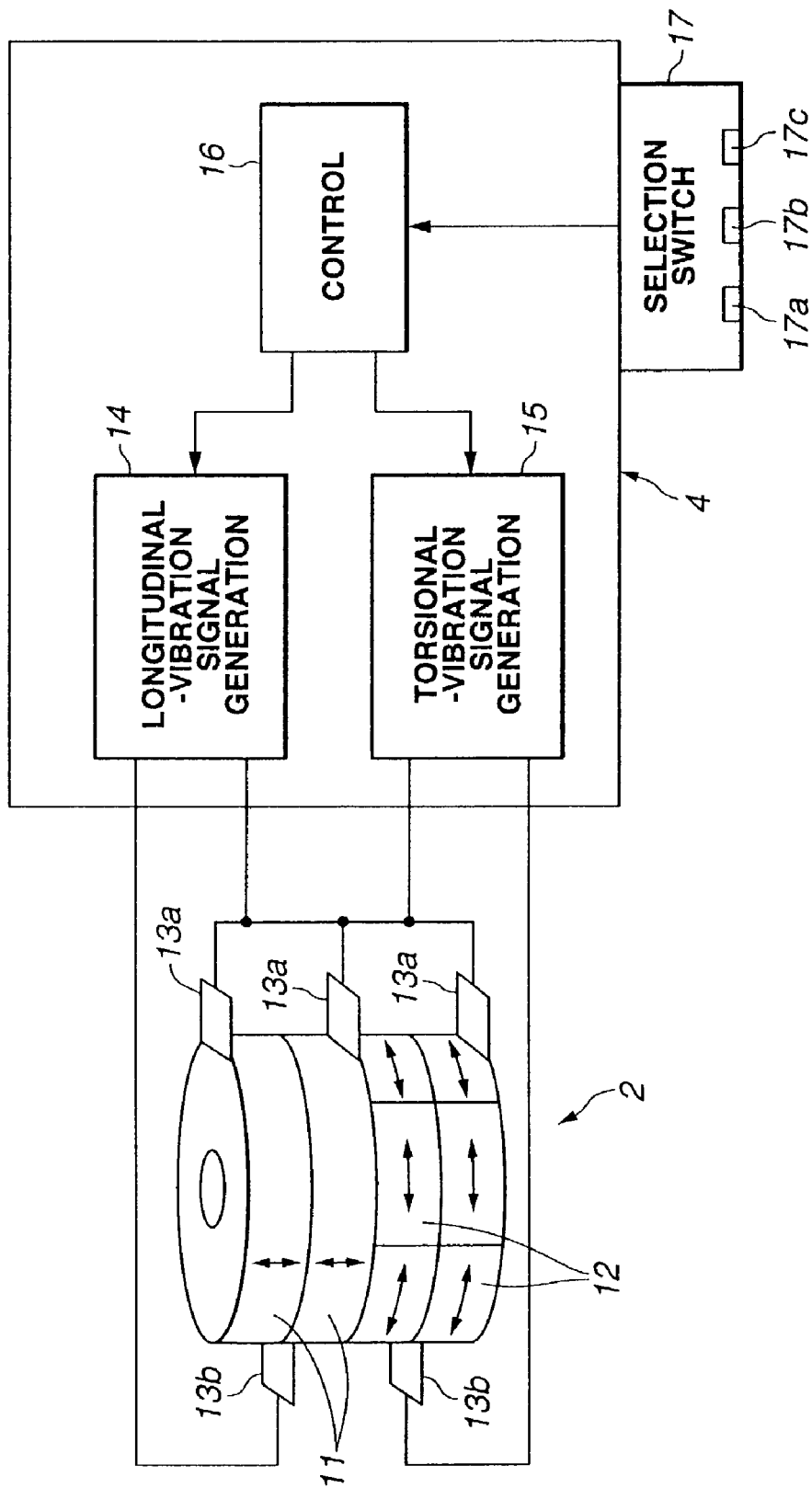

(A)

(B) LONGITUDINAL VIBRATION MODE (C) TORSIONAL VIBRATION MODE

FIG.12
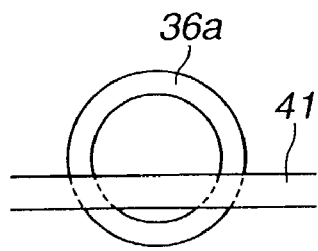
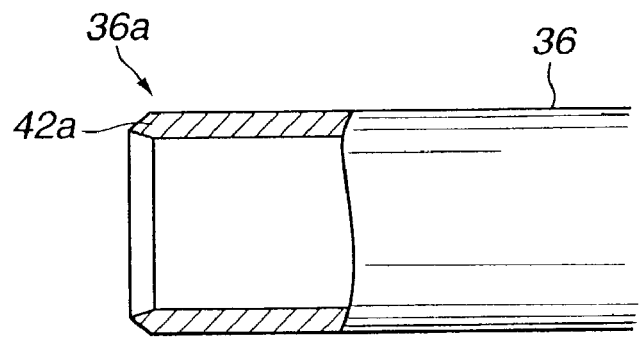
FIG.13A
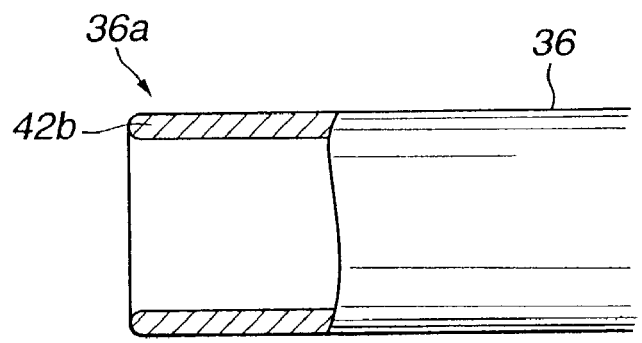
FIG.13B
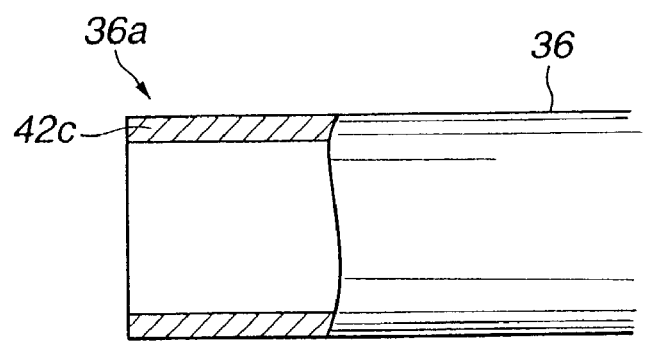
FIG.13C

ULTRASONIC CALCULUS TREATMENT APPARATUS

This application claims benefit of Japanese Application Nos. 2001-266251 and 2001-313013 filed on Sep. 3, 2001 and Oct. 10, 2001, respectively, the contents of which are incorporated by this reference.

BACKGROUND OF THE INVENTION

1. Field of the Invention

The present invention relates to a surgical apparatus using an ultrasonic transducer and, more particularly to an ultrasonic calculus treatment apparatus for breaking a calculus into pieces to remove the calculus.

2. Description of the Related Art

Various surgical apparatuses for endoscopically treating a calculus formed in a urinary passage or the like are being developed. Among the apparatuses, there is an ultrasonic lithotriptor (or an ultrasonic treatment apparatus) for transmitting ultrasonic vibrations to a probe (ultrasonic transmitting member) to break a calculus into pieces using the tip of the probe. Since the ultrasonic lithotriptor has characteristics that an ultrasonic energy acts only on a calculus and does not exert an influence on any biological tissue around the calculus, it is generally used. It is known that for the ultrasonic lithotriptor, a soft object such as biological tissue absorbs vibration and is not influenced by the vibration but a hard object such as a calculus is remarkably affected by a vibration energy.

Japanese Unexamined Patent Application Publication No. 62-298346 (Japanese Examined Patent Application Publication No. 06-087856) discloses an example. There is disclosed an apparatus in which a cover is disposed around a probe for transmitting ultrasonic vibrations in order to protect an inner portion of a channel of an endoscope, and the distal end of the probe is exposed from the end of the cover so that a calculus can be shattered.

In such an ultrasonic lithotriptor, as the probe for transmitting the ultrasonic vibration, a wire-shaped or pipe-shaped probe is used. Only substantially longitudinal vibration in the axial direction of ultrasonic vibration produced by an ultrasonic transducer is transmitted to the distal end of the probe, thereby shattering a calculus.

At this time, by only using the longitudinal vibration, the calculus may not be completely and efficiently shattered. For example, the calculus may be pierced in the longitudinal direction but it cannot be shattered. Accordingly, the calculus may not be easily removed from a body. Thus, it may take long time for treatment.

As disclosed in U.S. Pat No. 5,116,343, there is proposed a device in which vibration rotated about the axial direction, namely, twisted vibration (torsional vibration) is generated at the distal end of a probe to efficiently disintegrate a calculus. In the device, such a technique that torsional depressions are formed on the surface of a horn of a transducer or the distal end of the probe and simple longitudinal vibration produced by the transducer is transformed to torsional vibration at the distal end of the probe is disclosed.

However, the above-mentioned related art has a disadvantage in that the generation of the torsional vibration at the distal end of the probe is limited. In other words, when longitudinal vibration of the transducer has a phase in the extending direction, the vibration is rotated clockwise, and when the transducer has a phase in the contracting direction, the vibration is rotated counterclockwise. Namely, only the simple torsional vibration is generated.

Due to the structure, such a problem that the amplitude of the longitudinal vibration cannot be obtained enough occurs, resulting in a deterioration in efficiency of disintegration of a calculus.

U.S. Pat No. 6,161,545 discloses a surgical treatment instrument having an element for longitudinal vibration and an element for torsional vibration.

However, since means for freely changing and setting longitudinal vibration and torsional vibration is not disclosed, a function for effectively shattering a calculus may not be completed.

SUMMARY OF THE INVENTION

It is an object of the present invention to provide an ultrasonic calculus treatment apparatus in which the distal end of an ultrasonic transmitting member is vibrated longitudinally and torsionally with enough amplitude to effectively accomplish a calculus removing treatment such as lithotripsy.

Another object of the present invention is to provide an ultrasonic calculus treatment apparatus which can effectively perform a treatment for calculus removal in accordance with the shape or size of a calculus and an operating tool.

According to the present invention, there is provided an ultrasonic calculus treatment apparatus including:

an ultrasonic transducer having a first piezoelectric oscillator which can vibrate longitudinally in the axial direction and a second piezoelectric oscillator which can vibrate torsionally with respect to the longitudinal direction;

an ultrasonic transmitting member whose one end is connected to the ultrasonic transducer and in which an operating tool for treating an organism is disposed on the other end;

a first driving circuit for driving the first piezoelectric oscillator;

a second driving circuit for driving the second piezoelectric oscillator; and a control circuit for independently controlling the first and second driving circuits.

Accordingly, torsional vibration can be generated with enough amplitude at the distal end of the ultrasonic transmitting member so that treatment for calculus removal can be effectively performed by shattering the calculus.

BRIEF DESCRIPTION OF THE DRAWINGS

FIGS. 1 to 10C are related to a first embodiment according to the present invention, FIG. 1 showing a general configuration view of an ultrasonic lithotriptor of the first embodiment;

FIG. 3 is a block diagram showing an ultrasonic transducer and a signal generator;

FIG. 4 is a block diagram showing a longitudinal-vibration signal generation circuit and a torsional-vibration signal generation circuit;

FIG. 5 is an explanatory diagram of a process of generating a reference signal;

FIG. 6 is a diagram showing a situation in which an output frequency of a voltage control oscillator (VCO) varies in the range from a high frequency to a low frequency so as to track a frequency of the reference signal;

FIG. 7 is an explanatory diagram regarding resonance-point tracking of an apparatus main body;

FIG. 8 is a perspective view showing a vibration transmitting member and a distal tip according to a modification;

FIGS. 9A to 9G are diagrams showing representative examples of selectable vibration modes;

FIG. 10 includes a part (A) showing a schematic configuration view of the apparatus main body, a part (B) showing the vibration mode having intervals for longitudinal vibration, and a part (C) showing the vibration mode having intervals for torsional vibration;

FIGS. 11 to 13C are related to a second embodiment according to the present invention, FIG. 11 showing a perspective view of a handpiece of an ultrasonic tissue coagulation incision instrument according to the second embodiment;

FIG. 12 is a diagram showing a situation in which biological tissue is held by the distal end of a probe of an operating tool;

FIGS. 13A to 13C are diagrams each showing the shape of the distal end of the probe;

FIG. 15 is a block diagram of a section including a high-frequency power supply of the ultrasonic lithotriptor;

FIG. 16 is a timing chart for explaining the operation of a variable frequency oscillator of the third embodiment;

FIG. 17 is a flowchart for explaining the operation of the variable frequency oscillator of the third embodiment;

FIG. 18 is a block diagram showing a section for modulating a current of an ultrasonic transducer driving signal according to the third embodiment; and FIG. 19 includes diagrams showing a change in a current setting signal, a change in voltage of the ultrasonic transducer driving signal, and a change in current thereof upon modulating the ultrasonic transducer driving signal.

DESCRIPTION OF THE PREFERRED EMBODIMENTS

Embodiments according to the present invention will now be described hereinbelow with reference to the drawings.

A first embodiment according to the present invention will now be described with reference to FIGS. 1 to 10.

Figure 1:
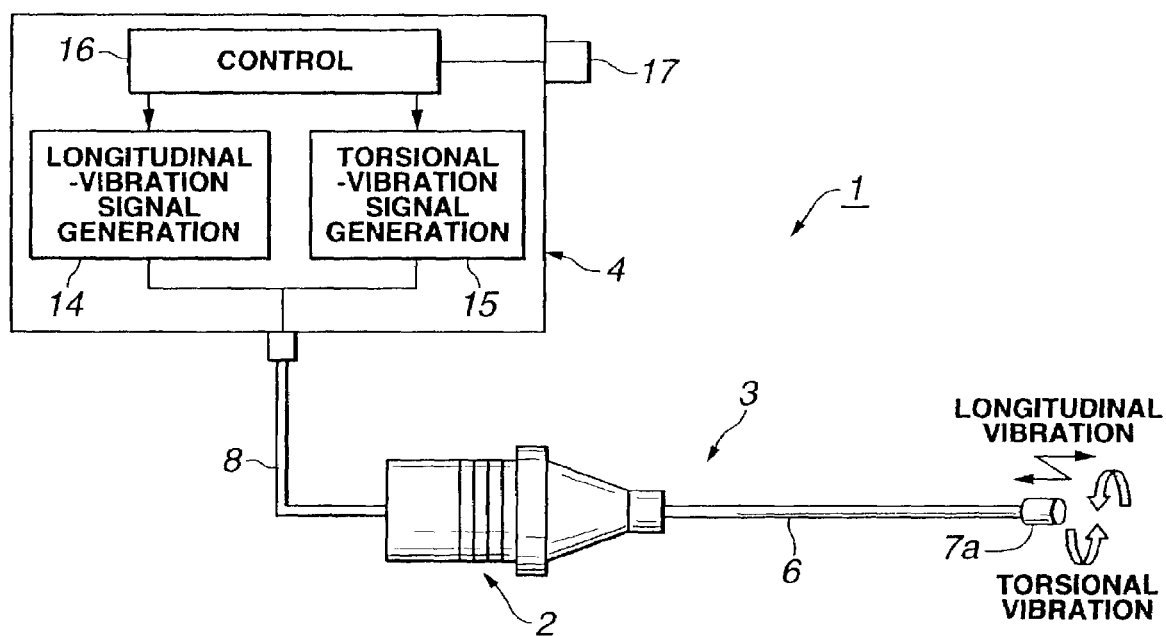

Referring to FIG. 1, according to the first embodiment of the present invention, an ultrasonic lithotriptor 1 comprises an ultrasonic transducer 2 for producing torsional vibration and longitudinal vibration, an ultrasonic lithotriptor main body (also called an apparatus main body) 3 including the ultrasonic transducer 2, and an ultrasonic driving signal generator (also called a signal generator) 4 for supplying a driving signal to produce ultrasonic waves to the apparatus main body 3. In FIG. 1, exterior components of the apparatus main body 3 are omitted.

The apparatus main body (also called a handpiece in an embodiment, which will be explained later) 3 has the ultrasonic transducer 2 disposed (in a grasping control section) at the rear end of the apparatus main body 3, a long vibration transmitting member 6, connected to the ultrasonic transducer 2, for transmitting ultrasonic vibration, a distal tip 7a disposed at the distal end of the vibration transmitting member 6, and a driving cable 8 connected to the ultrasonic transducer 2. The rear end of the driving cable 8 is detachably connected to the ultrasonic driving signal generator 4.

The signal generator 4 generates an ultrasonic transducer driving signal. The generated driving signal is supplied to the ultrasonic transducer 2. The ultrasonic transducer 2 produces longitudinal vibration and/or torsional vibration. The energy of the vibration is transmitted to the distal tip 7a through the vibration transmitting member 6. When the distal tip 7a comes into contact with a calculus, the ultrasonic vibration energy is applied to the calculus, thus shattering the calculus.

According to the present embodiment, the longitudinal vibration and the torsional vibration are produced so that the calculus can be broken effectively.

Figure 2A:
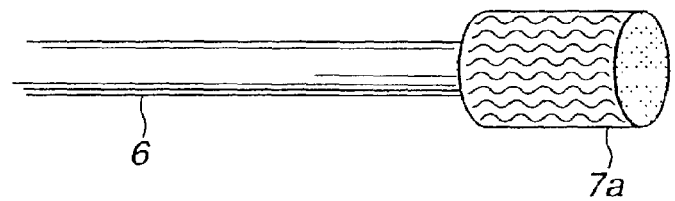
FIGS. 2A to 2C are schematic configuration views of distal tips.
Figure 2B:
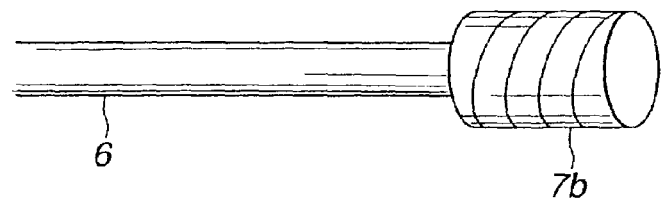
Figure 2C:
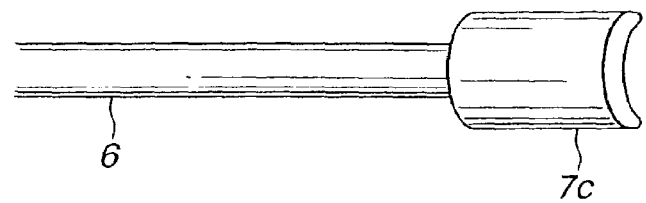

FIG. 2A shows the structure of the distal tip 7a and FIGS. 2B and 2C show modifications thereof.

FIG. 2A is an enlarged illustration of the distal tip 7a shown in FIG. 1. The distal tip 7a is an abrasive type. Projections and depressions are formed on the surface of the distal tip 7a like a file, thereby improving the operation for shaving the calculus.

A distal tip 7b shown in FIG. 2B is drill-shaped. In case of a calculus whose surface is very hard due to a uric acid component being deposited thereon, the distal tip 7b is vibrated torsionally and is further vibrated longitudinally to form a hole on the surface of the calculus. The hole facilitates the breaking of the calculus.

A distal tip 7c shown in FIG. 2C is chisel-shaped. For example, when a calculus is large, the distal tip 7c can scrape the calculus to break it into pieces.

In any of the distal tips, when only longitudinal vibration is performed, there is a disadvantage in that the calculus slips out toward the end of a probe (vibration transmitting member). When torsional vibration is performed, the calculus will unlikely slip away from the distal tip, thus vibration energy can be applied to the calculus.

FIG. 3 shows a configuration of the ultrasonic transducer 2 and a configuration of a section for allowing the ultrasonic transducer 2 to generate longitudinal vibration and torsional vibration.

According to the present embodiment, the ultrasonic transducer 2 comprises a plurality of stacked piezoelectric oscillators. In this case, the ultrasonic transducer 2 comprising four piezoelectric oscillators will now be explained.

For the four piezoelectric oscillators, for example, two longitudinal-vibration piezoelectric oscillators 11 which are polarized so as to generate longitudinal distortion and two torsional-vibration piezoelectric oscillators 12 which are polarized so as to generate torsional distortion are used.

Electrodes 13a and 13b are correspondingly disposed on both the surfaces of each piezoelectric oscillator. In order to easily connect a signal line to supply a driving signal to the electrode, a part of the electrode protrudes outwardly.

The signal generator 4 comprises a longitudinal-vibration signal generation circuit 14 for generating a driving signal for longitudinal vibration, a torsional-vibration signal generation circuit 15 for generating a driving signal for torsional vibration, and a control circuit 16 for controlling the generating operations of the generation circuits 14 and 15. A mode of vibration to be produced through the control circuit 16 can be selected by a selection switch 17.

The selection switch 17 has a mode selection button 17a for selecting the vibration mode, a period button 17b for changing or setting a period, and a power set button 17c for changing or setting a power level.

A driving signal generated by the longitudinal-vibration signal generation circuit 14 is supplied to each longitudinal-vibration piezoelectric oscillator 11, in which the electrodes 13a and 13b are attached to both the surfaces, through the signal line, so that longitudinal vibration expanding and contracting in the longitudinal direction is generated as shown by arrows in FIG. 3. The longitudinal vibration is transmitted to the distal tip 7a through the vibration transmitting member 6, thereby vibrating the distal tip 7a so as to expand and contract in the axial direction of the vibration transmitting member 6 as shown in FIG. 1.

A driving signal generated by the torsional-vibration signal generation circuit 15 is supplied to each torsional-vibration piezoelectric oscillator 12, in which the electrodes 13a and 13b are attached to both the surfaces, through the signal line, so that torsional vibration rotated in the circumferential direction as shown by arrows is generated. The torsional vibration is transmitted to the distal tip 7a through the vibration transmitting member 6, thereby vibrating the distal tip 7a so as to rotate about the axis of the vibration transmitting member 6 as shown in FIG. 1.

In accordance with a selection using the mode selection button 17a of the selection switch 17, the control circuit 16 controls so as to generate a signal for longitudinal vibration or a signal for torsional vibration, or simultaneously produce torsional vibration and longitudinal vibration. A generation period and a suspension period of vibration and the sum of the periods can be set by operating the period button 17b. A power level can be set by operating the power set button 17c.

Figure 4:
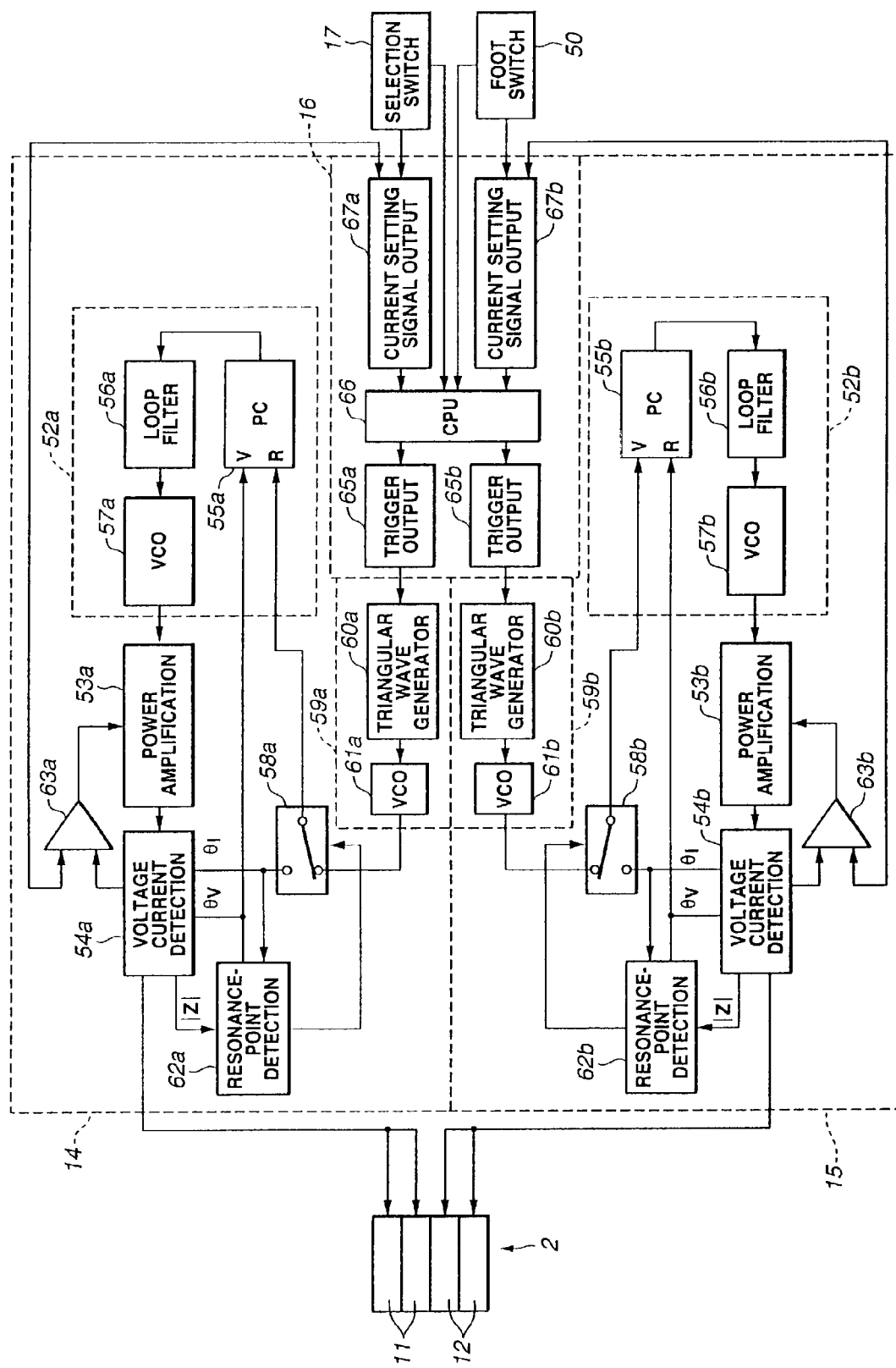

FIG. 4 specifically shows the configurations of the longitudinal-vibration signal generation circuit 14 and the torsional-vibration signal generation circuit 15 in FIG. 3.

The longitudinal-vibration signal generation circuit 14 shown in FIG. 4 has the same configuration as that of the torsional-vibration signal generation circuit 15.

In the longitudinal-vibration signal generation circuit 14, a power amplifier 53a amplifies an output signal of a phase-locked loop (PLL) 52a to generate a driving signal. The driving signal is supplied to each longitudinal-vibration piezoelectric oscillator 11 of the ultrasonic transducer 2. The longitudinal-vibration piezoelectric oscillator 11 is driven with the driving signal.

As the driving signal, a voltage phase signal θV which is supplied from a voltage and current detection circuit 54a to each longitudinal-vibration piezoelectric oscillator 11, a current phase signal θI according to vibration, an impedance |Z|, and a current |I| are detected.

The PLL 52a is constructed so as to supply an output of a phase comparator (PC) 55a to a voltage control oscillator (VCO) 57a, which can control its oscillation frequency using an applied voltage, through a loop filter 56a. An output of the VCO 57a is amplified by the power amplifier 53a and is then supplied to each longitudinal-vibration piezoelectric oscillator 11.

At this time, a differential amplifier 63a compares the current |I| according to the vibration of the apparatus main body 3 detected by the voltage and current detection circuit 54a with a current setting signal generated from a current setting signal output circuit 67a of the control circuit 16. An output of the differential amplifier 63a adjusts the amplification factor of the power amplifier 53a so that a current flowing through the longitudinal-vibration piezoelectric oscillator 11 is controlled at a value set by the current setting signal.

A level of the current setting signal generated from the current setting signal output circuit 67a can be set using a power set switch.

A variable input terminal (V) of the PC 55a is supplied with the voltage phase signal θV generated from the voltage and current detection circuit 54a. A reference input terminal (R) thereof is supplied with the current phase signal θI or a reference signal generated from a reference signal generation circuit 59a through a switching circuit 58a.

The reference signal generation circuit 59a comprises a so-called sweep oscillating circuit for sweeping a frequency from a high frequency fhigh, which is higher than a resonance frequency fra of the longitudinal-vibration piezoelectric oscillator 11, to a low frequency, which is lower than the resonance frequency fra, so as to include the resonance frequency fra.

The control circuit 16 comprises the current setting signal output circuit 67a, a CPU 66, and a trigger output circuit 65a. The current setting signal output circuit 67a and the trigger output circuit 65a are prepared for longitudinal vibration. A current setting signal output circuit 67b and a trigger output circuit 65b are prepared for torsional vibration.

When receiving a signal from a foot switch 50, the CPU 66 transmits a trigger signal (hereinbelow, referred to as an EN signal) to the reference signal generation circuit 59a and also transmits an EN signal to a reference signal generation circuit 59b.

When the reference signal generation circuit 59a receives the EN signal transmitted from the control circuit 16, a triangular wave generator 60a outputs a triangular voltage which varies in a predetermined value range. On the basis of the triangular voltage, a VCO 61a generates a reference signal (sweeping signal) whose frequency varies in a predetermined range.

Figure 5:
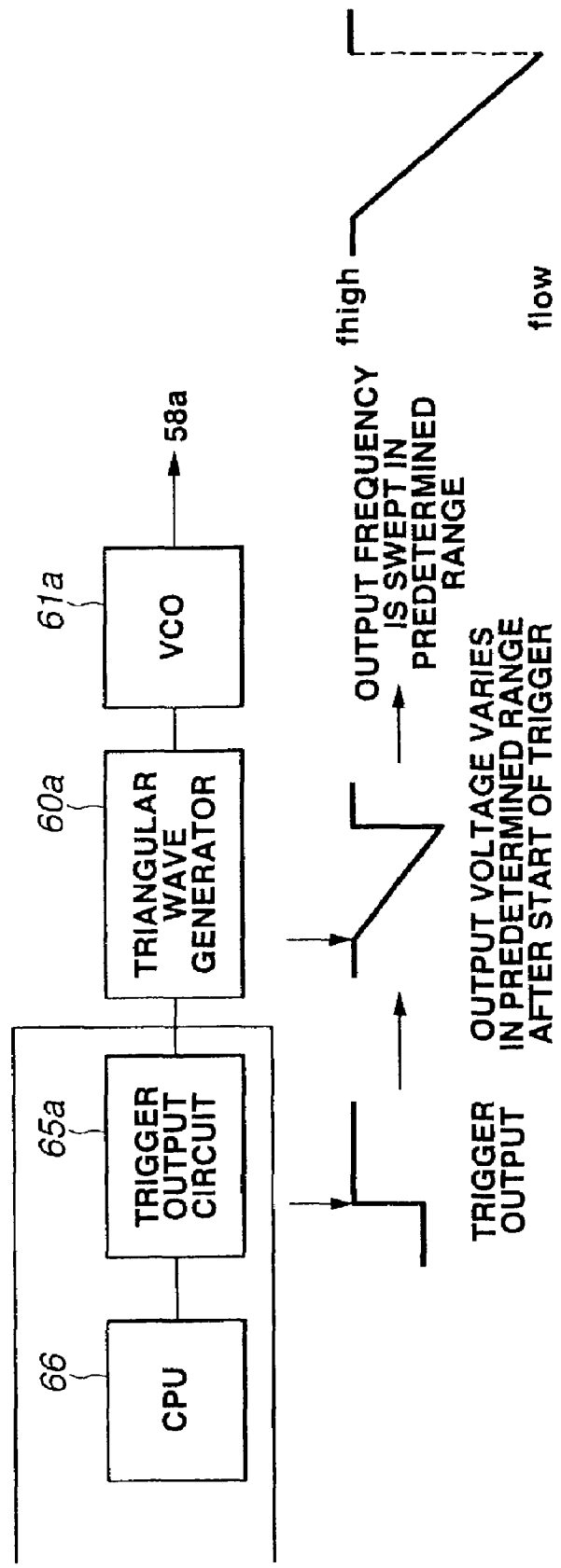

FIG. 5 is a diagram for explaining a process of generating the reference signal.

When receiving a signal from the foot switch 50 having a function serving as an ultrasonic output switch, the control circuit 16 controls the trigger output circuit 65a to generate a trigger output as shown in FIG. 5. After the start of the trigger, the triangular wave generator 60a outputs a triangular voltage which varies in the predetermined range. On the basis of the output voltage, the VCO 61a generates a reference signal whose output frequency varies in the predetermined range and then supplies the signal to the switching circuit 58a.

Figure 6:
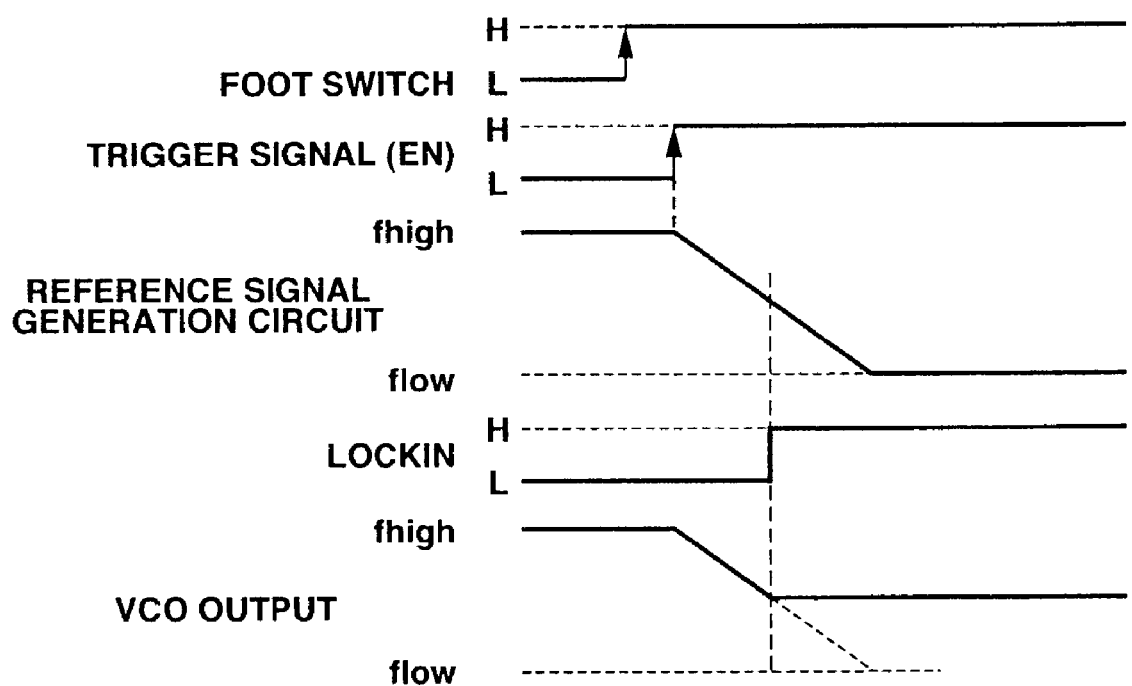

An output frequency of the VCO 57a tracks the frequency of the reference signal and varies from the high frequency fhigh to the low frequency flow as shown in FIG. 6.

Figure 7:
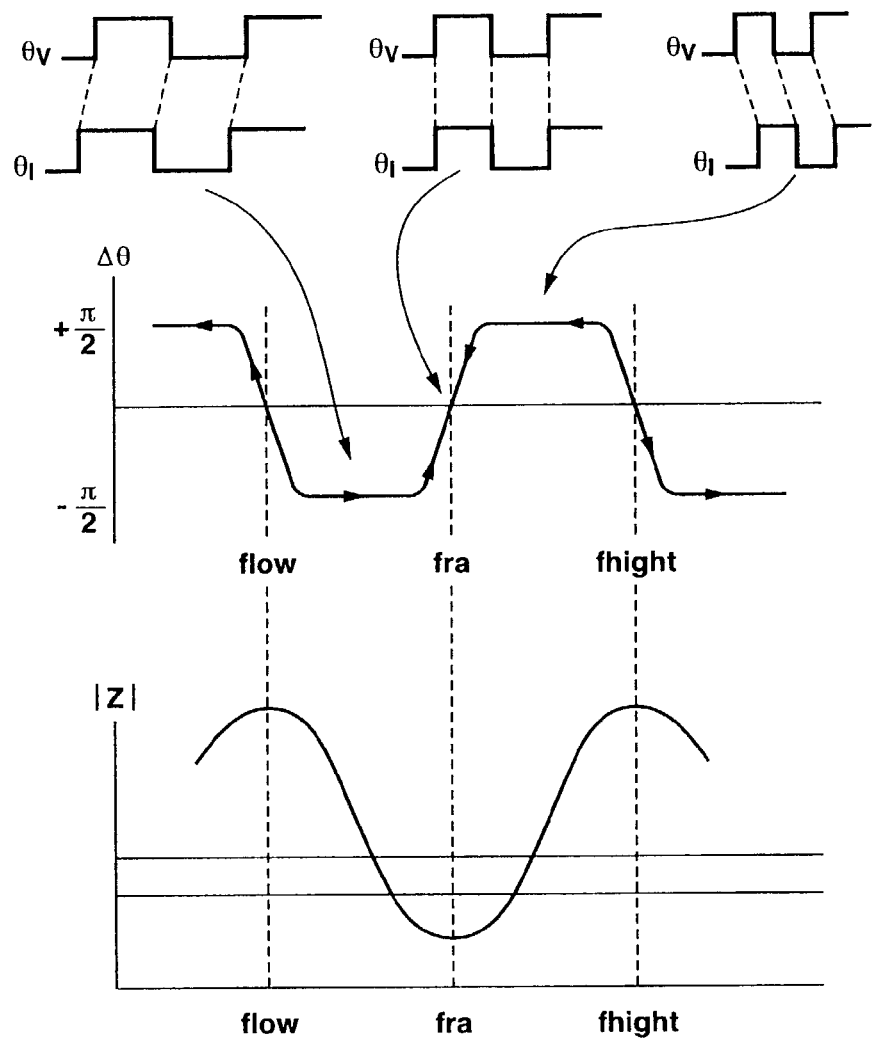

In this case, as shown in FIG. 7, when the output frequency matches the resonance frequency fra of the longitudinal-vibration piezoelectric oscillator 11, a phase difference between θI and θV is equal to 0°, an output (LOCKIN) of a resonance-point detection circuit 62a changes, e.g., from a level "L" (low) to a level "H" (high), and the switching circuit 58a is switched so that the current phase signal θI as the driving signal is input to the input terminal R of the PC 55a. Consequently, the PLL 52a is controlled so that the phase of θI always matches that of θV, and the longitudinal-vibration piezoelectric oscillator 11 is driven so that the above matched phase coincides with the resonance frequency fra of the longitudinal-vibration piezoelectric oscillator 11. That is, resonance-point tracking is performed.

The specific configuration and operation of the longitudinal-vibration signal generation circuit 14 have been described. The configuration and the operation of the torsional-vibration signal generation circuit 15 shown in FIG. 4 are substantially similar to those of the longitudinal-vibration signal generation circuit 14.

In other words, the torsional-vibration signal generation circuit 15 drives the torsional-vibration piezoelectric oscillator 12 so that an output frequency of a VCO 57b matches a resonance frequency frb of the torsional-vibration piezoelectric oscillator 12, namely, resonance-point tracking is performed.

Accordingly, in FIG. 4, components of the torsional-vibration signal generation circuit 15 are designated by the same reference numerals as those of the longitudinal-vibration signal generation circuit 14 but each reference numeral has a reference symbol b in place of a reference symbol a. The explanation is omitted.

By the selecting operation of the selection switch 17, as shown in FIGS. 9A to 9G which will be described later, the mode of the combination of the longitudinal vibration and the torsional vibration to be produced can be set freely so that the apparatus main body (handpiece) 3 can be vibrated in the mode suitable for treatment such as lithotripsy whereby a calculus is removed from an organism.

As understood from the above structure, in the ultrasonic lithotriptor 1 according to the present embodiment, the lithotriptor main body (also called the handpiece) has the ultrasonic transducer 2 therein. The transducer 2 comprises a first piezoelectric oscillator for longitudinal vibration and a second piezoelectric oscillator for torsional vibration. The ultrasonic lithotriptor 1 further has the ultrasonic transmitting member for transmitting ultrasonic vibration produced by the ultrasonic transducer 2 to the operating tool at the distal end, a first driving signal generation circuit for driving the first piezoelectric oscillator, a second driving signal generation circuit for driving the second piezoelectric oscillator, and the control circuit 16 for independently controlling the first and second driving signal generation circuits.

On the basis of the selecting operation of the selection switch 17, the mode of the longitudinal vibration and/or the torsional vibration to be produced, the period, and the power level can be selected freely.

The operation of the ultrasonic lithotriptor 1 with this configuration will now be described.

First, the presence of a calculus in an organ (not shown) is confirmed using a rigid endoscope. Then, the vibration transmitting member 6 (a sheath in which the vibration transmitting member 6 is inserted) of the ultrasonic lithotriptor 1 is inserted through a channel formed in the rigid endoscope or a trocar. The vibration transmitting member 6 is usually inserted into the sheath.

Under observation by the endoscope, the distal tip 7a is pressed against the calculus and an ultrasonic driving signal is supplied to the ultrasonic transducer 2. In this case, any of the distal tips 7a to 7c, which is the most effective in shattering the calculus, is used. In this instance, the explanation will be made on the assumption that the distal tip 7a is used.

By operating the mode selection button 17a or the like of the selection switch 17 in accordance with the size and the shape of the calculus, a longitudinal vibration mode of merely longitudinally vibrating the distal tip 7a, a torsional vibration mode of merely torsionally vibrating the distal tip 7a, or a longitudinal and torsional vibration mode of longitudinally and torsionally vibrating the distal tip 7a is selected. Then, the foot switch 50 serving as an ultrasonic output switch is turned on.

The ultrasonic transducer 2 is vibrated on the basis of the selected mode, period, and power level. The vibration is transmitted to the distal tip 7a through the vibration transmitting member 6, so that the calculus to which the distal tip 7a is pressed against can be scraped and broken.

According to the present embodiment, the distal tip 7a can be vibrated by not only the longitudinal vibration but also the torsional vibration or the longitudinal and torsional vibration. Accordingly, the distal tip can be vibrated in the vibration mode effective in lithotripsy in accordance with the size and the shape of the calculus and the type of any of the distal tips 7a to 7c used for the lithotripsy. Breaking and removing the calculus can be accomplished with high efficiency.

For example, the following control can be realized: Until the distal tip 7a catches the calculus, the distal tip 7a is torsionally vibrated in order to hit a calculus. After catching, the longitudinal vibration is applied to the distal tip 7a so that the calculus is broken with a high energy.

Figure 8:
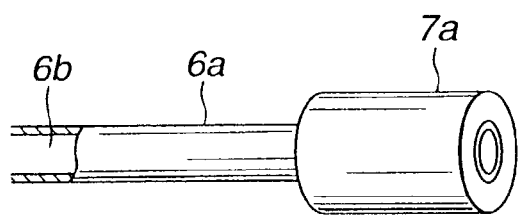

The vibration transmitting member 6 is not limited to a solid rod-shaped one but a pipe-shaped vibration transmitting member 6a as shown in FIG. 8 can be used. In this case, preferably, the distal tip 7a has an opening communicating with a hollow 6b of the pipe-shaped vibration transmitting member 6a because the distal tip 7a is arranged on the periphery at the distal end of the pipe-shaped vibration transmitting member 6a.

In this case, the following configuration may be used: The hollow 6b at the proximal end of the pipe-shaped vibration transmitting member 6a is connected to an absorbing unit. The absorbing unit absorbs the calculus broken into pieces by the distal tip 7a at the distal end of the pipe-shaped vibration transmitting member 6a. Consequently, the pieces can be easily discharged through the hollow 6b of the pipe-shaped vibration transmitting member 6a.

By selecting the mode using the mode selection button 17a of the selection switch 17, as shown in FIGS. 9A and 9B, only the longitudinal vibration mode or only the torsional vibration mode can be selected. Furthermore, when the period button 17b or the power set button 17c is operated, the mode of the combination of the longitudinal vibration and the torsional vibration and a period of the mode can be selected and set as shown by representative examples in FIGS. 9C to 9F. In FIGS. 9A to 9F, the abscissa axis denotes time t and the ordinate axis denotes the power level.

FIG. 9A shows a vibration mode when only the longitudinal vibration is selected. In the mode shown in FIG. 9A, only the longitudinal vibration is intermittently performed. FIG. 9A shows a case where an output period is set to Ta1, an output suspension period is set to Ta2, and the vibration is periodically generated.

FIG. 9B shows a mode when only the torsional vibration is selected in place of the longitudinal vibration shown in FIG. 9A. Namely, in the mode of FIG. 9B, only the torsional vibration is intermittently performed. In this case, an output period is set to Tb1, an output suspension period is set to Tb2, and the vibration is periodically generated.

FIGS. 9C to 9F show modes of combinations of the longitudinal vibration and the torsional vibration. FIG. 9C shows a case where the longitudinal vibration is synchronized with the torsional vibration so that they are alternately generated. In FIG. 9C, an output period Ta3 is equivalent to an output period Tb3. Although the longitudinal vibration is synchronized with the torsional vibration so that they are alternately generated in FIG. 9C, the vibrations may be synchronized with each other so that the output period Ta3 matches the output period Tb3.

FIG. 9D shows a mode in which the longitudinal vibration is continuous and the torsional vibration is intermittently generated. An output period of the torsional vibration is set to Tb4 and an output suspension time thereof is set to Tb5.

FIG. 9E shows a mode obtained by reversing the states of the longitudinal vibration with the torsional vibration in FIG. 9D. An output period of the longitudinal vibration is set to Ta4 and an output suspension period thereof is set to Ta5.

FIG. 9F shows a mode similar to that of FIG. 9E but an output period Ta6 of the longitudinal vibration and an output suspension period Ta7 thereof are changed. Namely, the output period and the suspension period of the longitudinal vibration are changed.

Figure 9:
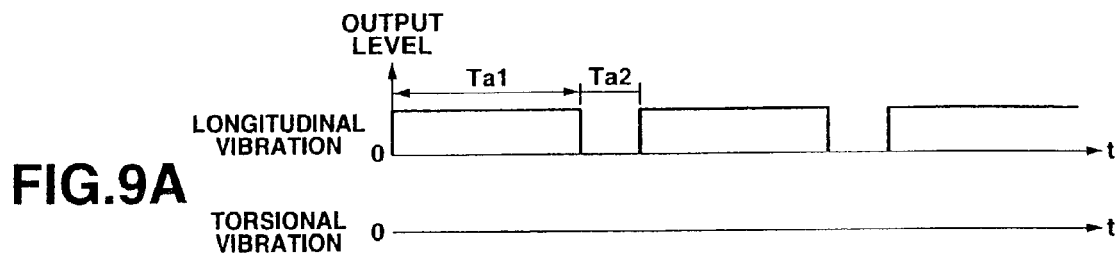

FIG. 9G shows a mode similar to that of FIG. 9 except that the power set button 17c is operated to increase the power level of the longitudinal vibration.

As mentioned above, according to the present embodiment, the mode of the longitudinal vibration and/or the torsional vibration, the period, and the power level can be variably set using the selection switch 17. Consequently, the mode appropriate for shattering a calculus can be selected and set.

Figure 10:
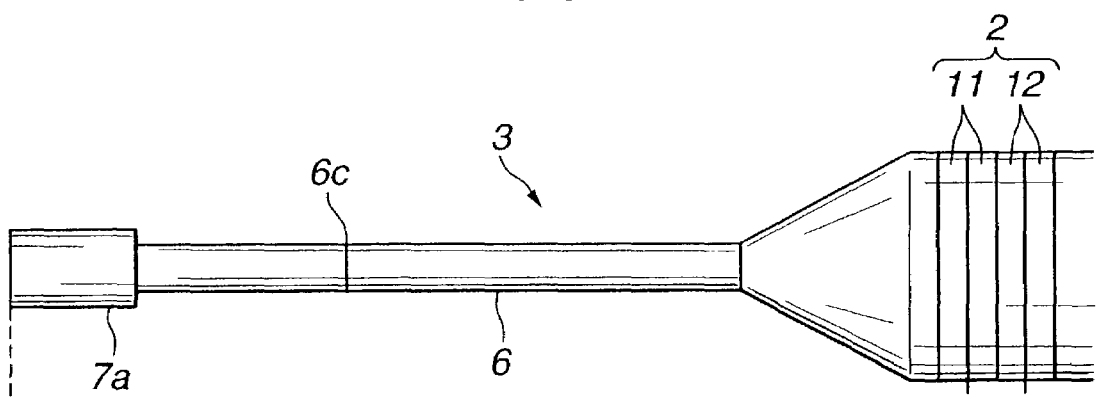

According to the present embodiment, for example, when the ultrasonic transducer 2 comprising the longitudinal-vibration piezoelectric oscillators 11 and the torsional-vibration piezoelectric oscillators 12 is fixed to the rear end of the vibration transmitting member 6 as shown in a part (A) of FIG. 10 and the longitudinal-vibration piezoelectric oscillators 11 produce longitudinal vibration, and the torsional-vibration piezoelectric oscillators 12 produce torsional vibration, the respective vibration modes produce vibration so as to form standing waves as shown in parts (B) and (C) of FIG. 10.

In other words, in case of the longitudinal vibration mode as shown in the part (B) of FIG. 10, the length of the vibration transmitting member 6 and the resonance frequency fra of the longitudinal-vibration piezoelectric oscillator 11 are set so that a node of the vibration is formed in the longitudinal-vibration piezoelectric oscillators 11 and a loop of the vibration is formed at the distal tip 7a along the longitudinal direction of the vibration transmitting member 6.

In case of the torsional vibration mode as shown in the part (C) of FIG. 10, the length of the vibration transmitting member 6 and the resonance frequency frb of the torsional-vibration piezoelectric oscillator 12 are set so that a node of the vibration is formed in the torsional-vibration piezoelectric oscillators 12 and a loop of the vibration is formed at the distal tip 7a along the longitudinal direction of the vibration transmitting member 6.

According to the present embodiment, therefore, a portion which an operator or the like holds is inhibited from vibrating extensively and the distal tip 7a can be vibrated widely, so that a function to shatter a calculus can be improved and the operability of the apparatus can also be increased.

When the distal tip 7a is detachably connected to the distal end of the transmitting member 6 and is replaced by another one, a connecting portion 6c using, e.g., a screw is set near the node of the vibration in each of the longitudinal vibration and the torsional vibration so that the connecting portion 6c is hardly influenced by the vibration.

In the part (A) of FIG. 10, when the positions of the longitudinal-vibration piezoelectric oscillators 11 are substantially equivalent to those of the torsional-vibration piezoelectric oscillators 12 in the axial direction of the vibration transmitting member 6, the two reference signal generation circuits 59a and 59b shown in FIG. 4 may be integrated into one common circuit.

A second embodiment of the present invention will now be described with reference to FIGS. 11 to 13C.

Figure 11:
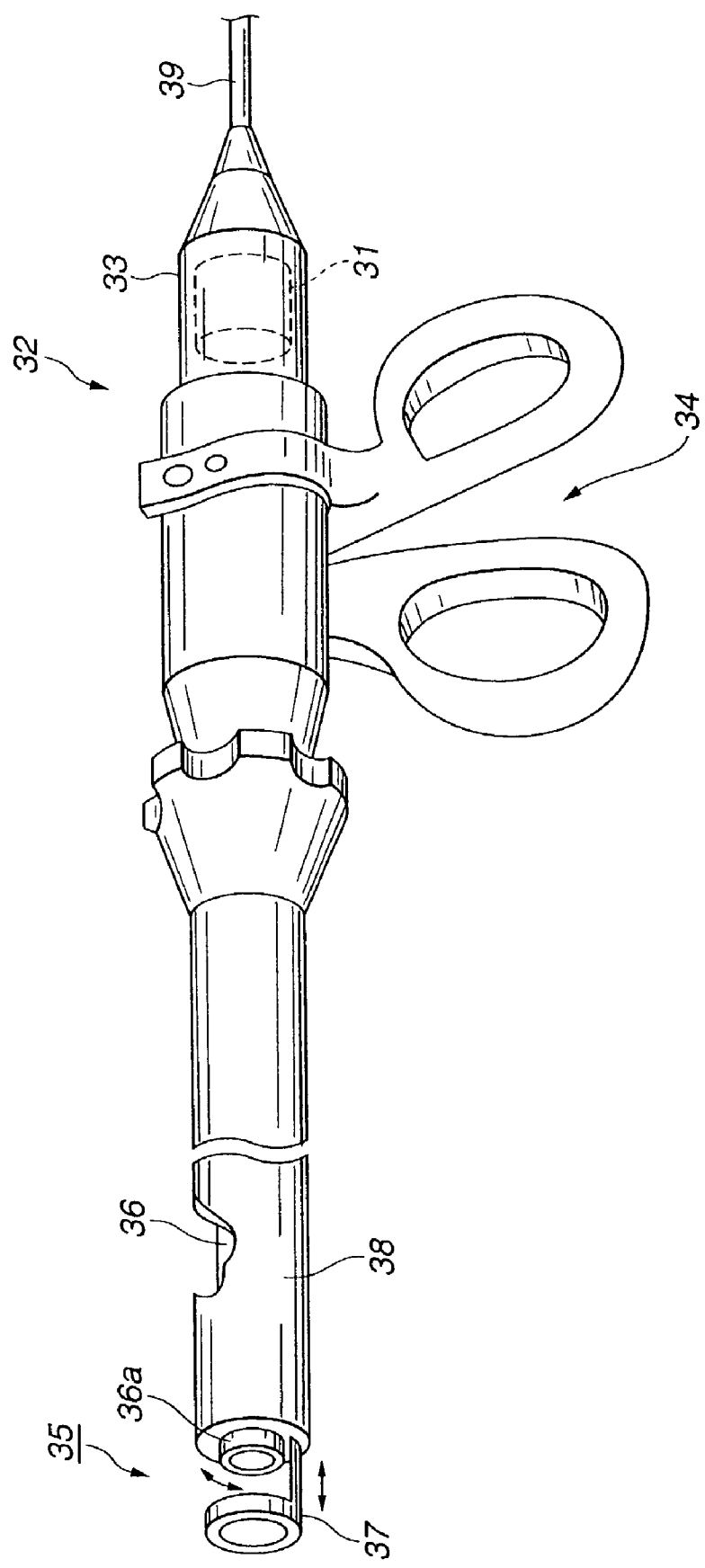

FIG. 11 shows a handpiece 32 in an ultrasonic tissue coagulation incision apparatus having an ultrasonic vibrator 31 for producing torsional vibration therein.

The handpiece 32 comprises: a transducer 33 having the torsional vibrator 31; a handle 34 which is arranged near the transducer 33 and which an operator holds with their hand and then operates; a probe 36 serving as an ultrasonic transmitting member for transmitting ultrasonic vibration produced by the torsional vibrator 31 to an operating tool 35 at the distal end of the probe; a movable grasping tool 37 which comes into contact with or released from the end surface of the probe 36 by operating the handle 34; a coupling rod (not shown) for coupling the movable grasping tool 37 with the handle 34; and a sheath 38 covering the probe 36.

The transducer 33 is connected to a signal generator (not shown) for generating a driving signal through a cable 39 which transmits the driving signal to drive the torsional vibrator 31 built in the transducer.

When the operator holds the handle 34 so that handle elements approach each other, the movable grasping tool 37 is moved backward so as to approach a probe distal end 36a. When the operator releases the handle 4, the movable grasping tool 37 is moved away from the probe distal end 36a.

Accordingly, as shown in FIG. 11, tissue to be coagulated or incised is inserted between the movable grasping tool 37 and the probe distal end 36a which are separated from each other. When the operator holds the handle 34 so that the handle elements approach each other, the tissue serving as a treatment target can be grasped.

Torsional vibration produced by the torsional vibrator 31 disposed in the transducer 33 is transmitted to the probe distal end 36a through the probe 36, and a vibration energy is then applied to the tissue sandwiched between the probe distal end 36a and the movable grasping tool 37 so that treatment such as coagulation or incision can be performed.

As shown in FIG. 12, biological tissue 41 such as a blood vessel desired to be coagulated or incised is sandwiched between the movable grasping tool 37 and the probe distal end 36a, the handle 34 is held so that the handle elements approach each other, and the torsional vibration is applied. Accordingly, the biological tissue 41 generates heat due to frictional heat, so that the tissue can be cut by a pinching force while the tissue is being coagulated.

The probe distal end 36a may be shaped into any of the forms shown in FIGS. 13A to 13C.

Referring to FIG. 13A, when the probe distal end 36a has sharp edges 42a, the probe 36 has a high efficiency for incision.

As shown in FIG. 13B, when the probe distal end 36a has rounded edges 42b, the probe 36 has a balanced function for incision and coagulation.

Referring to FIG. 13C, when the probe distal end 36a has a flat end surface 42c without any edge, the probe 36 has a high efficiency for coagulation. As mentioned above, the operation level can be varied.

In the foregoing first embodiment, since the direction in which ultrasonic vibration is transmitted is the same as that in which tissue is grasped, a coefficient of static friction is reduced due to the vibration. The grasped tissue may slip out and the distal end may also slip. According to the present embodiment, the above case does not occur and tissue can be tightly grasped.

In other words, the tissue serving as a treatment target can be held as a component to be vibrated in the direction perpendicular to the insertion axis without slipping away from the distal end. An advantage in that the occurrence of cavitation is reduced along the probe distal end is also obtained.

In the present embodiment, longitudinal vibration and torsional vibration can also be generated independently.

An ultrasonic surgical instrument of a third embodiment of the present invention will now be described. The ultrasonic surgical instrument has a characteristic ultrasonic driving signal generator.

An outline of the present embodiment will now be described. According to the present embodiment, a handpiece is first driven by a driving signal with a frequency generated by a variable frequency oscillator, and a phase difference between a voltage phase signal θV as the driving signal detected by a voltage and current detection circuit and an output signal from the variable frequency oscillator is checked.

When the phase difference is equivalent to 0°, the operation of the handpiece is switched so that the handpiece is driven by an output signal of a PLL which operates by comparing the phase of the voltage phase signal θV as the handpiece driving signal with the phase of a current phase signal θI, thereby tracking a resonance frequency. In this case, the variable frequency oscillator comprises a digital circuit.

In order to modulate vibration applied to the handpiece, a current of the driving signal is compared with a current setting signal to change the amplification factor of the driving signal, and the current setting signal is switched between a high value and a low value at predetermined intervals in a portion where the driving signal is controlled at a constant current, thereby modulating the current.

Figure 14:
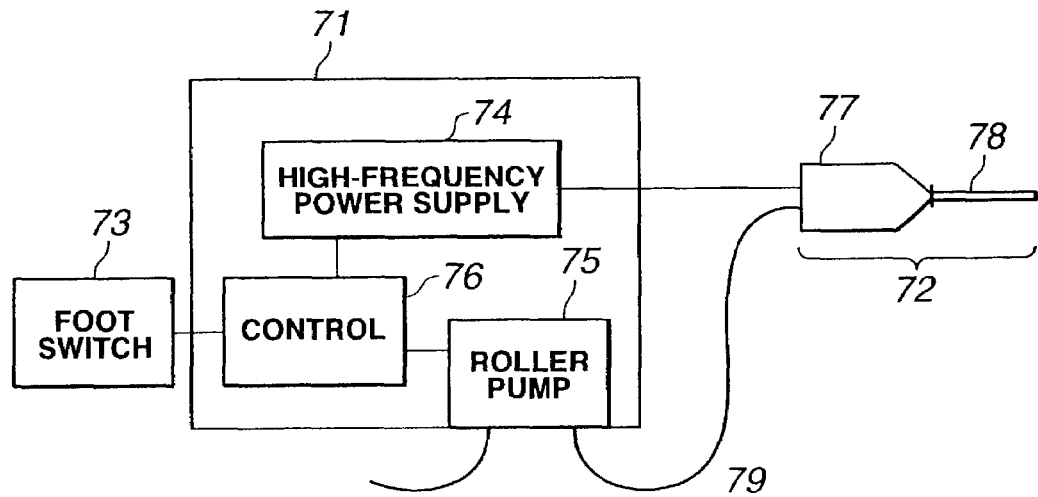
FIGS. 14 to 19 are related to a third embodiment according to the present invention, FIG. 14 showing a block diagram of an ultrasonic lithotriptor of the third embodiment.

The present embodiment will now be described in detail with reference to FIGS. 14 to 19. FIG. 14 shows a configuration of a general ultrasonic lithotriptor. For the whole configuration, the lithotriptor comprises an ultrasonic lithotriptor main body 71, a handpiece 72, and a foot switch 73. The ultrasonic lithotriptor main body 71 comprises a high-frequency power supply 74 serving as an ultrasonic driving signal generator for supplying a driving signal to an ultrasonic transducer, which will be described hereinbelow, a roller pump 75 for permitting a tube 79 connected to the handpiece 72 to absorb a refluxing liquid and broken pieces of a calculus, and a control circuit 76 for controlling the high-frequency power supply 74 and the roller pump 75 in accordance with a signal supplied from the foot switch 73.

The handpiece 72 comprises an ultrasonic transducer 77 for transducing the driving signal supplied from the high-frequency power supply 74 into mechanical vibration, and a breaking probe 78 comprising a hollow rod. The probe 78 is connected to the ultrasonic transducer 77 and is inserted into a patient's body through a channel of a rigid endoscope in order to break a calculus with the ultrasonically vibrated distal end thereof and to absorb the refluxing liquid and pieces of the broken calculus.

The characteristics of the present embodiment will now be described hereinbelow with respect to a configuration of the high-frequency power supply 74 of the ultrasonic lithotriptor.

Figure 15:
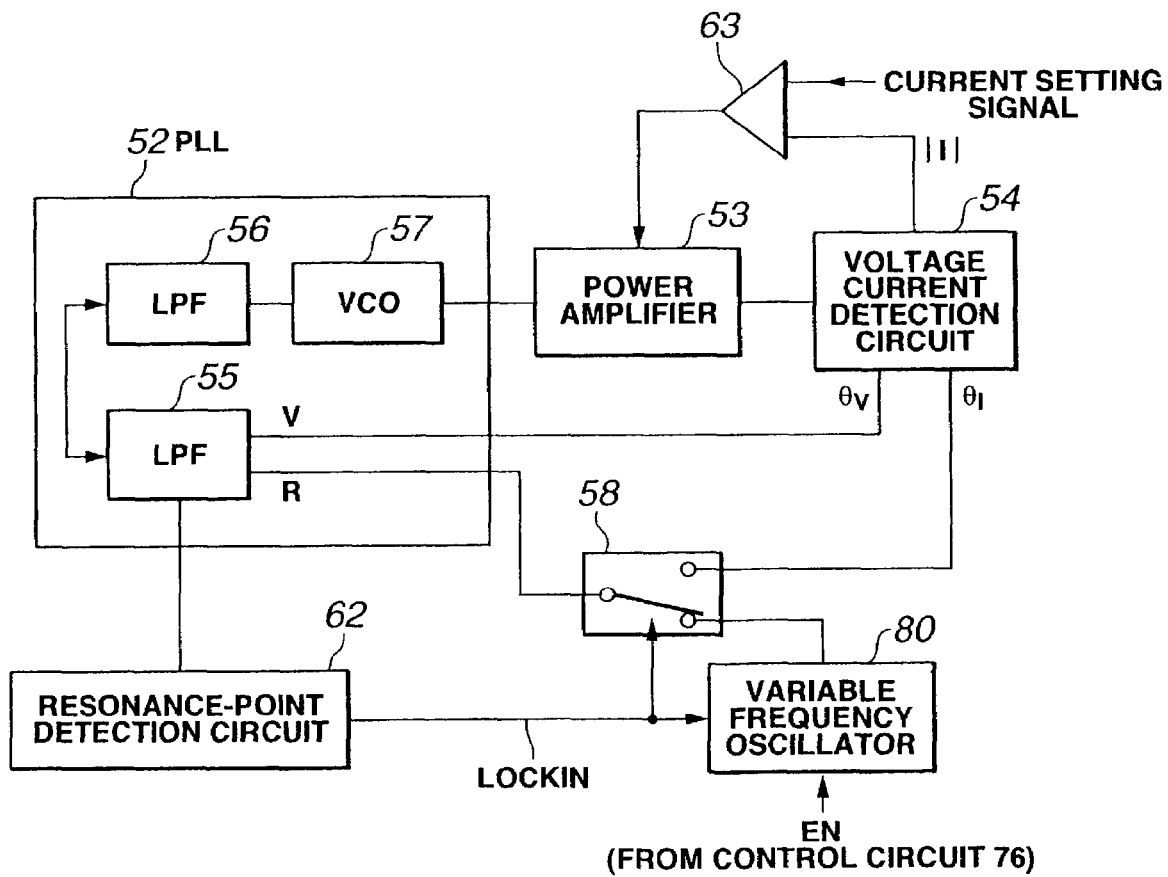

FIG. 15 shows the configuration of the power supply 74 according to the present embodiment. The following things are different from the configuration of the longitudinal-vibration driving signal generation circuit 14 or the torsional-vibration driving signal generation circuit 15 shown in FIG. 4. The reference signal generator 59a (or 59b) is replaced with a variable frequency oscillator (first variable oscillator) 80. On the basis of an output of the phase comparator (PC) 55a (or 55b), the foregoing resonance-point detection circuit 62a (or 62b) determines a resonance point when a phase difference between the voltage phase signal θV as the driving signal and an output signal of the variable frequency oscillator 80 is equivalent to 0°.

In the following explanation, a case where driving is performed only by longitudinal vibration or torsional vibration will be described. Accordingly, each reference symbol a or b in FIG. 4 is omitted and the explanation will now be made.

Figure 16:
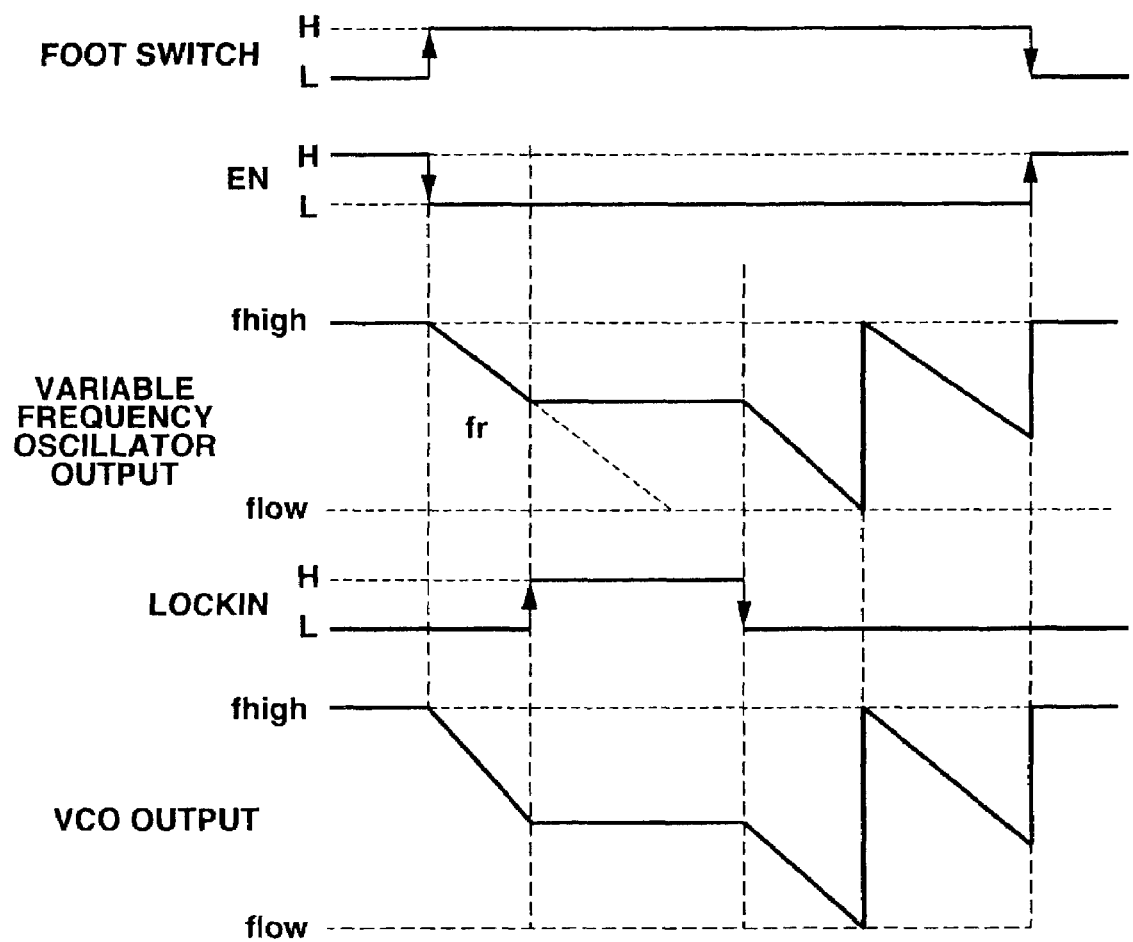

The operation of the variable frequency oscillator 80 according to the present embodiment will now be described hereinbelow with reference to a timing chart of FIG. 16.

The variable frequency oscillator 80 has a period counter for counting a period in order to output a signal having a set frequency, and a step counter whose value is related to a counted value per period in order to change a frequency to be output from the oscillator 80 over time.

When the falling edge of an EN signal supplied from the control circuit 76 is detected, the variable frequency oscillator 80 resets the period counter and the step counter to switch an output to another level at the start time of each step (period counter=0) and at a half period time. While the EN signal is at the level "L" and a LOCKIN signal is at the level "L", the value of the step counter is increased every time each step is completed. Consequently, the frequency to be output sequentially changes. When the step counter indicates the maximum value, the step counter is reset, the frequency of the output signal is reset to an initial frequency, and such changing is repeated.

When the resonance-point detection circuit 62 detects a resonance point and the LOCKIN signal generated from the circuit 62 goes to the level "H", the step counter is not updated even after counting by the period counter is completed. Accordingly, the frequency of the output signal of the variable frequency oscillator 80 is fixed to a frequency obtained upon detecting the resonance point.

The output frequency of the variable frequency oscillator 80 substantially matches a resonance frequency of the handpiece 72. Accordingly, when the LOCKIN signal goes to the level "H" to switch the switching circuit 58, the frequency of the voltage phase signal θV substantially matches that of the current phase signal θI, the PLL 52 compares the frequencies of the signals with each other to track the resonance point of the handpiece 72.

Since a frequency supplied to the PLL 52 before switching the switching circuit 58 substantially matches a frequency supplied to the PLL 52 after the switching, there is no failure in tracking the resonance point.

While the EN signal is at the level "H", the value of the step counter is set to the initial value. Consequently, the variable frequency oscillator 80 continuously outputs a signal with the initial frequency.

Figure 17:
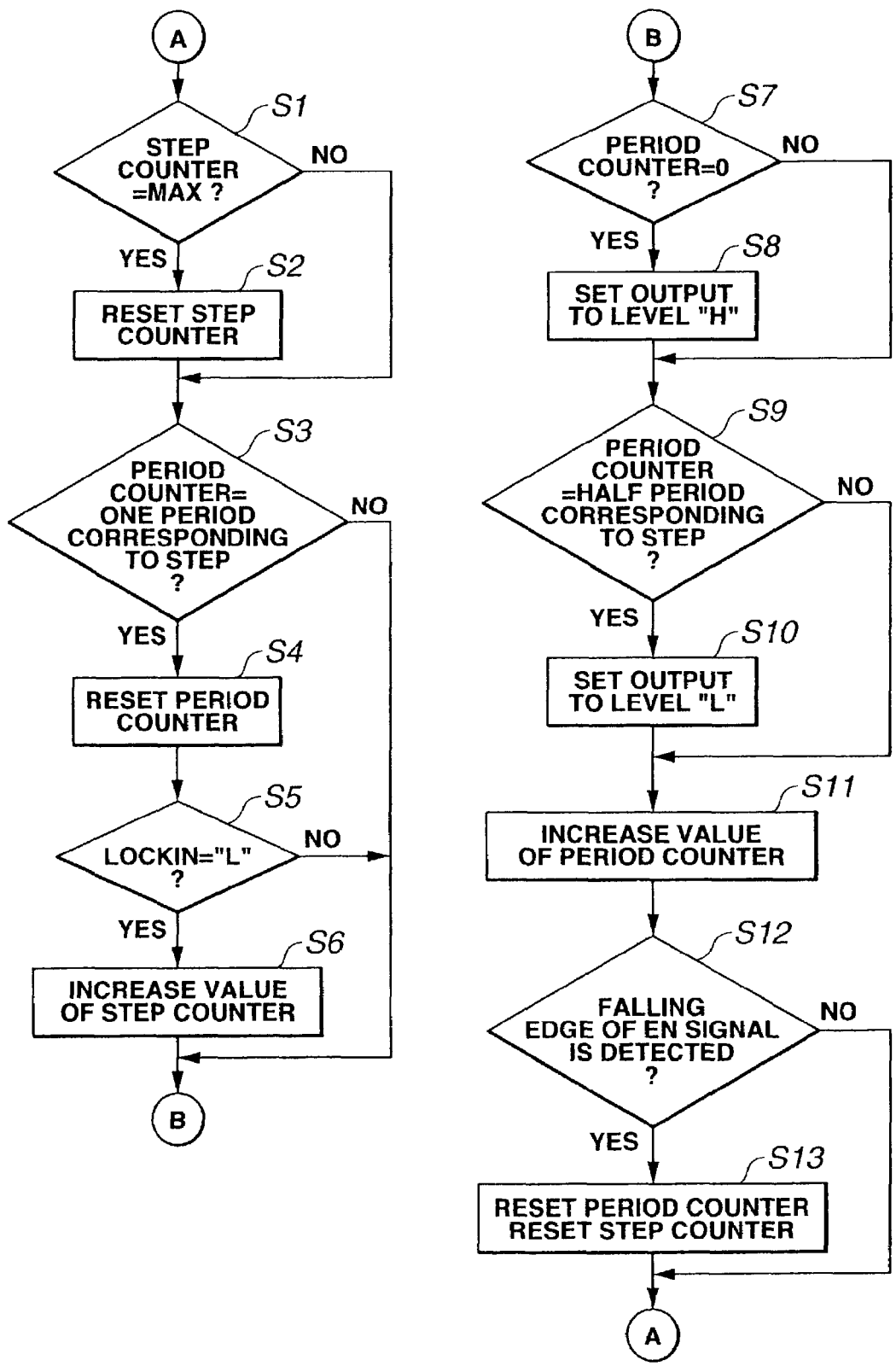

FIG. 17 is a flowchart showing the operation of the variable frequency oscillator 80. First, whether the step counter denotes the maximum value is determined (step S1). If NO, the operation proceeds to step S3. If YES, the step counter is reset (step S2) and the operation then proceeds to step S3.

In step S3, whether the period counter denotes one period corresponding to a step is determined. If NO, the operation proceeds to step S7. If YES, the period counter is reset (step S4) and whether the LOCKIN signal is at the level "L" is determined (step S5). If NO in step S5, the operation proceeds to step S7. If YES, the value of the step counter is increased (step S6) and the operation proceeds to step S7.

In step S7, whether the period counter denotes zero is determined. If NO, the operation proceeds to step S9. If YES, the LOCKIN output is set to the level "H" (step S8) and the operation then proceeds to step S9. In step S9, whether the period counter denotes a half period corresponding to the step is determined. If NO, the operation proceeds to step S11. If YES, the LOCKIN output is set to the level "L" (step S10) and the operation proceeds to step S11.

In step S11, the value of the period counter is increased. Subsequently, whether the falling edge of the EN signal is detected is determined (step S12). If NO, the operation proceeds to step S1. If YES, the period counter and the step counter are reset (step S13) and the operation then proceeds to step S1.

Figure 18:
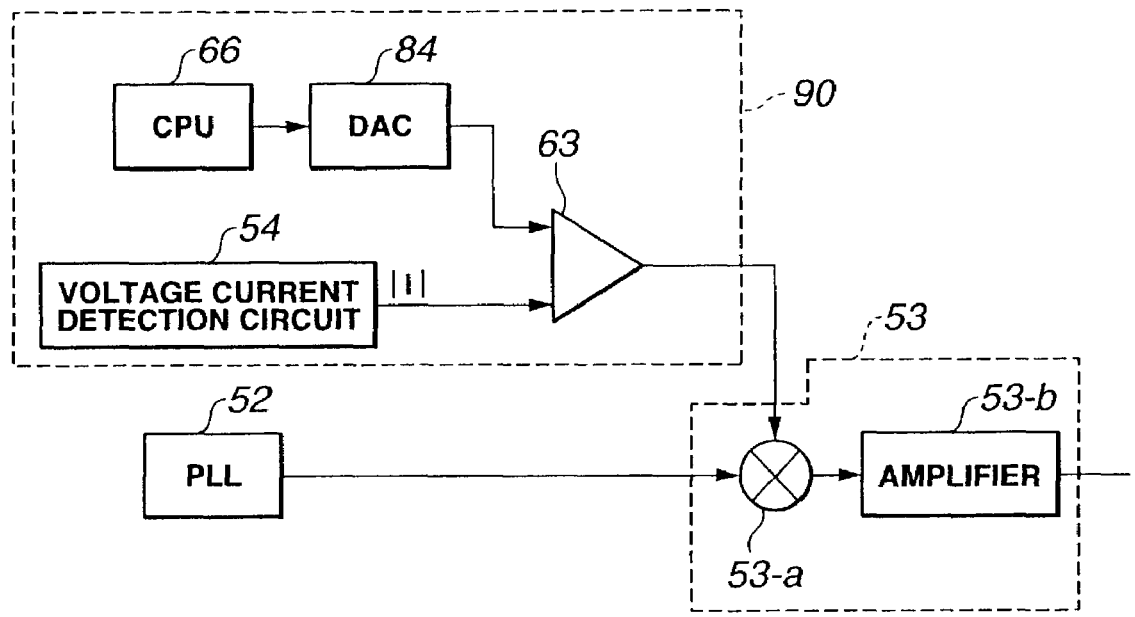

FIG. 18 is a block diagram showing a section for modulating a current of the ultrasonic transducer driving signal in the present embodiment according to the present invention.

A section (not shown in FIG. 15) for generating the current setting signal is a DA converter (DAC) 84. The CPU 66 controls an output of the DAC 84. A constant current control unit 90 comprises CPU 66, the DAC 84, the differential amplifier 63, and the voltage and current detection circuit 54. The power amplifier 53 is divided into a multiplier 53-a whose amplification factor varies according to the output of the differential amplifier 63 and an amplifier 53-b whose amplification factor is fixed.

When an output voltage (current setting signal) of the DAC 84 is held constant, a current detected by the voltage and current detection circuit 54 is compared with the value of the current setting signal, and the amplification factor of the multiplier 53-a is adjusted according to a difference therebetween to change the amplitude of a signal output from the PLL 52, thereby keeping a current of the ultrasonic transducer driving signal constant.

According to the present embodiment, the CPU 66 has a plurality of current setting signals (set values) to be supplied to the differential amplifier 63, and repetitively sets and changes the set values. In this case, the CPU 66 repetitively sets and changes the set values for a period that is a constant multiple of one period of the handpiece driving frequency.

In other words, the CPU 66 updates a register of the DAC 84 at a predetermined time interval (for example, 5 ms) to change the value of the current setting signal, thereby modulating the ultrasonic transducer driving signal which is controlled so as to have a current corresponding to the current setting signal. Consequently, the breaking probe 78, which vibrates in proportion to a current, produces vibration having a frequency other than the resonance frequency, thereby preventing the breaking probe 78 from being clogged with broken pieces accumulated in a portion corresponding to a node of the vibration.

Figure 19:
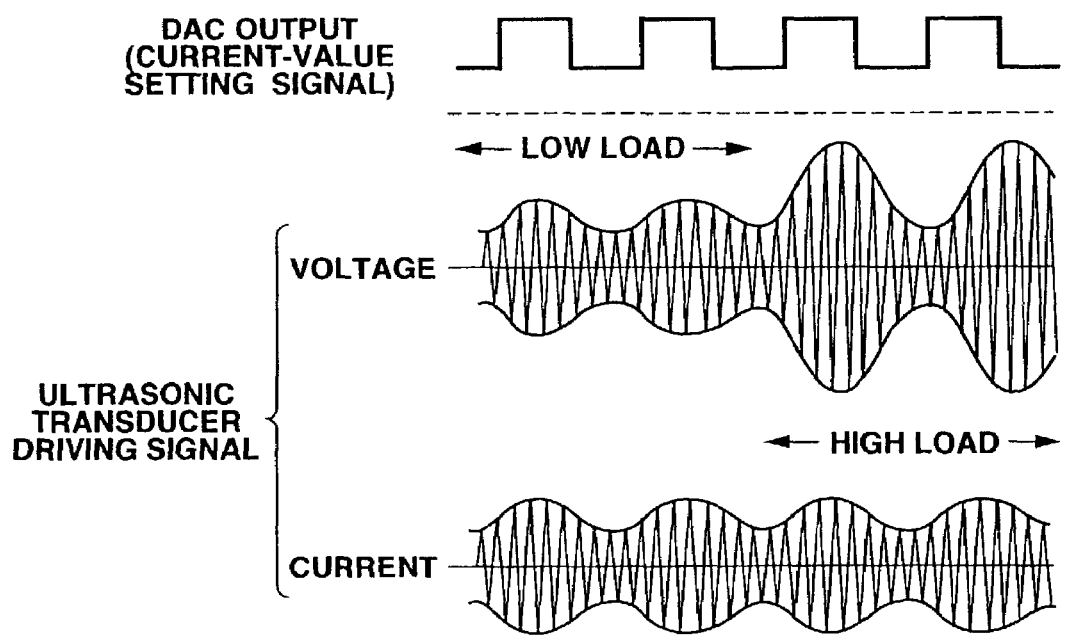

FIG. 19 shows a variation in the current setting signal (DAC output) and variations in the voltage and the current of the ultrasonic transducer driving signal at that time.

As a frequency for modulation at that time, a value of about 1/100 of the resonance frequency of the handpiece 72 or less is preferable. When the ultrasonic transducer driving signal to be output is modulated, it is preferable that the magnitude of the driving signal be not lower than the minimum magnitude at which the voltage phase signal and the current phase signal can be detected by the voltage and current detection circuit 54 and a low current be equal to 1/4 of a high current or more upon modulation.

On the other hand, while the modulation control is being performed, the constant current control is operated. When the breaking probe is strongly pressed against the calculus, a load is increased, resulting in an increase in impedance. In this case, the voltage is adjusted so that the current of the driving signal is in a predetermined value range as shown in FIG. 19. The vibration of the breaking probe 78 varies in the same way as in case of a small load. The vibration of the breaking probe 78 is proportional to the current of the driving signal. Accordingly, a constant breaking capacity can be obtained irrespective of the load.

According to the above-mentioned embodiment, the output of the variable frequency oscillator 80 for sweeping a frequency in a predetermined range is supplied to the phase comparator (PC) 55 of the PLL 52 and is then fixed to the resonance frequency of the handpiece 72 including the combination of the ultrasonic vibrator and the breaking probe 78, so that it is possible to immediately shift to the resonance point tracking.

The output value of the DAC 84 for outputting the current setting voltage for the constant current control circuit is switched to another value at a predetermined time interval using interruption by the CPU, so that a stable breaking capacity can be maintained. Furthermore, the driving current to drive the handpiece 72 is modulated to produce vibration having a frequency other than the resonance frequency in accordance with a sharp change in vibration amplitude of the breaking probe 78, so that pieces of the broken calculus shattered by the breaking probe 78 and then absorbed can be prevented from accumulating in the portion corresponding to the node of the vibration with the resonance frequency.

According to the present embodiment, therefore, the ultrasonic surgical instrument which can realize certain start of ultrasonic oscillation of the breaking probe and prevent the probe from being clogged can be provided.

Also, having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An ultrasonic calculus treatment apparatus for performing treatment using ultrasonic vibration, comprising:
   an ultrasonic transducer section including a plurality of ultrasonic transducers that longitudinally vibrate in the direction of an axis and torsionally vibrate in a torsional direction with respect to the axis, respectively, to treat biological tissue;
   a first oscillator for generating a driving signal to drive at least one of the plurality of ultrasonic transducers in the ultrasonic transducer section, wherein the first oscillator is adapted to generate, as the driving signal, a first driving signal and a second driving signal for driving the plurality of ultrasonic transducers, respectively;
   a phase information detection circuit for detecting phase information of the driving signal supplied from the first oscillator to the at least one of the ultrasonic transducers in the ultrasonic transducer section;
   a PLL control circuit for controlling an oscillation frequency of the first oscillator so as to be equivalent to a resonance frequency of at least one of the plurality of ultrasonic transducers on the basis of a result of the detection by the phase information detection circuit;
   a second oscillator for generating a sweep signal swept in a predetermined frequency range including the resonance frequency;
   a switching circuit for selecting the sweep signal supplied from the second oscillator or a detection signal supplied from the phase information detection circuit and then outputting the selected signal to the PLL control circuit; and
   a control section adapted to separately control the longitudinal vibration and the torsional vibration.

2. The apparatus according to claim 1, wherein the second oscillator comprises a digital circuit.

3. The apparatus according to claim 1, wherein the control section comprises a selection switch adapted to select a combination of the longitudinal vibration and the torsional vibration.

4. The apparatus according to claim 3, wherein the selection switch is adapted to select a mode of only the longitudinal vibration, a mode of only the torsional vibration, and a mode of the combination of the longitudinal vibration and the torsional vibration.

5. The apparatus according to claim 3, wherein the selection switch is adapted to change a period of the longitudinal vibration and a period of the torsional vibration.

6. The apparatus according to claim 1, wherein the control circuit comprises an output setting circuit adapted to control the first oscillator to allow changing an amplitude of the longitudinal vibration and an amplitude of the torsional vibration.

* * * * *